United States Patent
Martin et al.

(12)

(10) Patent No.: US 6,352,577 B1
(45) Date of Patent: Mar. 5, 2002

(54) MICROCHANNEL LAMINATED MASS EXCHANGER AND METHOD OF MAKING

(75) Inventors: Peter M. Martin; Wendy D. Bennett; Dean W. Matson, all of Kennewick; Donald C. Stewart, Richland; Monte K. Drost, Pasco; Robert S. Wegeng; Joseph M. Perez, both of Richland; Xiangdong Feng; Jun Liu, both of West Richland, all of WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/564,476

(22) Filed: May 3, 2000

Related U.S. Application Data

(60) Division of application No. 08/938,228, filed on Sep. 26, 1997, now Pat. No. 6,129,973, which is a continuation-in-part of application No. 08/606,155, filed on Feb. 23, 1996, now Pat. No. 5,811,062, which is a continuation-in-part of application No. 08/546,329, filed on Oct. 20, 1995, now abandoned, which is a continuation-in-part of application No. 08/282,663, filed on Jul. 29, 1994, now Pat. No. 5,611,214.

(51) Int. Cl.$^7$ .............................................. B01D 53/22
(52) U.S. Cl. ................... 96/4; 96/108; 96/243; 96/326
(58) Field of Search ................. 95/45–54; 96/4–14, 96/108, 135, 243, 322, 326

(56) References Cited

U.S. PATENT DOCUMENTS

| | | | | | |
|---|---|---|---|---|---|
| 3,520,803 | A | * | 7/1970 | Iaconelli ....................... | 96/7 X |
| 3,564,819 | A | * | 2/1971 | Neulander et al. ............... | 96/7 |
| 3,614,856 | A | * | 10/1971 | Sanz et al. .................... | 96/6 X |
| 3,619,986 | A | * | 11/1971 | Mormont et al. ................. | 96/7 |
| 3,735,562 | A | * | 5/1973 | Mousseau, Jr. et al. .......... | 96/6 |

(List continued on next page.)

FOREIGN PATENT DOCUMENTS

| | | |
|---|---|---|
| EP | 754492 A2 | 1/1997 |
| WO | WO91/17286 | 11/1991 |
| WO | PCT/US96/16546 | 4/1997 |

*Primary Examiner*—Robert H. Spitzer
(74) *Attorney, Agent, or Firm*—Paul W. Zimmerman; Frank S. Rosenberg

(57) ABSTRACT

The present invention is a microchannel mass exchanger having a first plurality of inner thin sheets and a second plurality of outer thin sheets. The inner thin sheets each have a solid margin around a circumference, the solid margin defining a slot through the inner thin sheet thickness. The outer thin sheets each have at least two header holes on opposite ends and when sandwiching an inner thin sheet. The outer thin sheets further have a mass exchange medium. The assembly forms a closed flow channel assembly wherein fluid enters through one of the header holes into the slot and exits through another of the header holes after contacting the mass exchange medium.

10 Claims, 8 Drawing Sheets

U.S. PATENT DOCUMENTS

| | | | |
|---|---|---|---|
| 3,797,202 A | * 3/1974 | Neulander et al. | 96/5 |
| 3,823,457 A | 7/1974 | Staas et al. | 29/890.039 |
| 3,856,270 A | 12/1974 | Hemker | 366/340 |
| 3,925,037 A | * 12/1975 | Ward, III et al. | 96/5 |
| 4,048,993 A | * 9/1977 | Dobritz | 96/4 X |
| 4,119,408 A | 10/1978 | Matson | 422/169 |
| 4,187,086 A | * 2/1980 | Walmet et al. | 96/5 X |
| 4,239,728 A | * 12/1980 | Stenberg et al. | 96/7 X |
| 4,268,279 A | 5/1981 | Shindo et al. | 55/16 |
| 4,516,632 A | 5/1985 | Swift et al. | 165/167 |
| 4,869,849 A | 9/1989 | Hirose et al. | 261/78.2 |
| 4,999,107 A | * 3/1991 | Guerif | 96/7 X |
| 5,016,707 A | 5/1991 | Nguyen | 165/167 |
| 5,126,045 A | * 6/1992 | Kohlheb et al. | 96/4 X |
| 5,160,673 A | 11/1992 | Wollbeck et al. | 264/45.1 |
| 5,178,210 A | 1/1993 | Guillet et al. | 165/111 |
| 5,225,080 A | * 7/1993 | Karbachsch et al. | 96/4 X |
| 5,250,263 A | 10/1993 | Manz | 422/81 |
| 5,281,254 A | 1/1994 | Birbara et al. | 95/44 |
| 5,316,568 A | * 5/1994 | Brown | 96/4 X |
| 5,455,401 A | 10/1995 | Dumais et al. | 219/121.52 |
| 5,534,328 A | 7/1996 | Ashmead et al. | 428/166 |
| 5,580,452 A | 12/1996 | Lin | 210/321.74 |
| 5,620,616 A | 4/1997 | Anderson et al. | 219/121.52 |
| 5,788,742 A | 8/1998 | Sugimoto et al. | 95/46 |
| 5,811,062 A | * 9/1998 | Wegeng et al. | 422/129 |
| 5,895,572 A | * 4/1999 | Joulin et al. | 96/4 X |
| 5,904,424 A | 5/1999 | Schwesinger et al. | 366/336 |
| 6,126,723 A | * 10/2000 | Drost et al. | 96/4 |
| 6,129,973 A | * 10/2000 | Martin et al. | 428/166 |
| 6,171,374 B1 | * 1/2001 | Barton et al. | 96/7 |

\* cited by examiner

Fluid In    Fluid Out    *Fig. 2a*

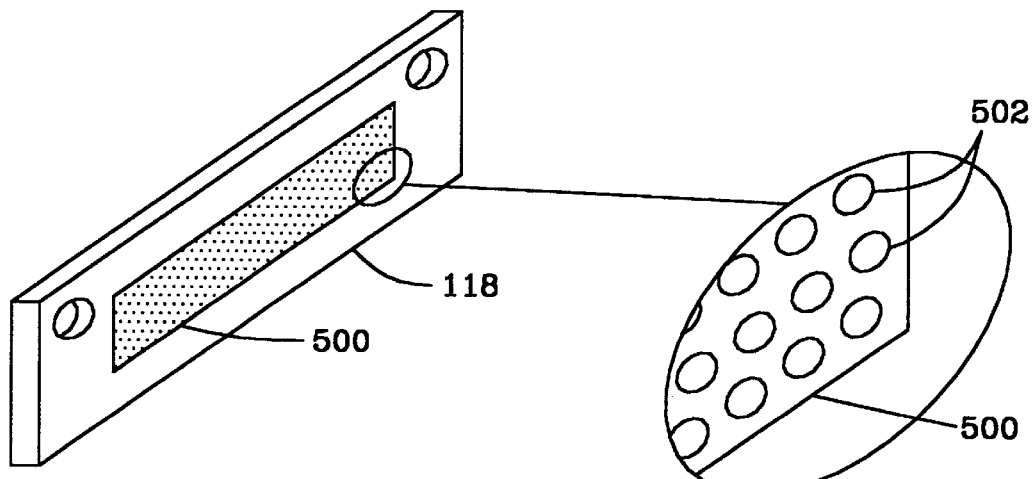
*Fig. 5a*
*Fig. 5b*
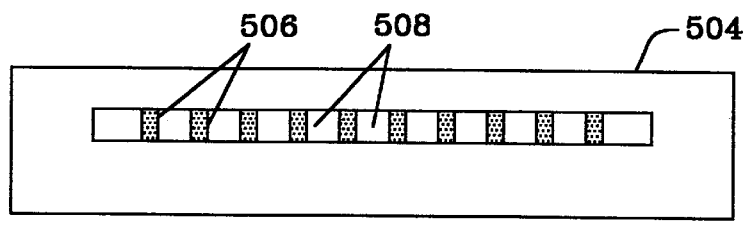
*Fig. 5c*
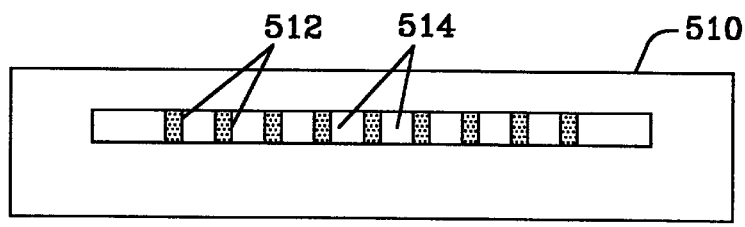
*Fig. 5d*

MICROCHANNEL LAMINATED MASS EXCHANGER AND METHOD OF MAKING

CROSS-REFERENCE TO RELATED APPLICATIONS

This application is a divisional of U.S. patent application Ser. No. 08/938,228, filed Sep. 26, 1997, now U.S. Pat. No. 6,129,973, incorporated herein by reference, which was a continuation-in-part of application Ser. No. 08/606,155 filed Feb. 23, 1996, now U.S. Pat. No. 5,811,062, which was a continuation-in-part of Ser. No 08/546,329, filed Oct. 20, 1995, abandoned, which was a continuation-in-part of U.S. patent application Ser. No. 08/282,663 filed Jul. 29, 1994, now U.S. Pat. No. 5,611,214.

This invention was made with Government support under Contract DE-AC06 76RLO 1830 awarded by the U.S. Department of Energy. The Government has certain rights in the invention.

FIELD OF THE INVENTION

The present invention relates generally to a mass exchanger and method of making a mass exchanger. As used herein, the term "mass exchanger" is defined as an apparatus wherein solute molecules in a solvent pass from the solvent to a mass transfer medium, or particles in a fluid pass from the fluid to a mass transfer medium.

BACKGROUND OF THE INVENTION

Mass transfer has been well known and studied for many years. Examples include chemical separations, catalytic reactions wherein a species contacts a catalyst surface and exchanges mass with another species to form a compound, i.e. catalytic reaction. Exemplary apparati include kidney dialysis machines for separations wherein the mass transfer medium is a tube through which certain compounds pass because of a concentration gradient from the fluid within the tube to the fluid exterior to the tube. An example of a catalyzed mass transfer apparatus is a catalytic converter to reduce pollutants in automobile exhaust. Disadvantages of large scale mass transfer have been recognized and efforts made to use small scale mass transfer.

Separations and catalyzed reactions have been shown in microscale apparati as well. U.S. Pat. No. 5,534,328 to Ashmead et al. show a laminated structure wherein flow channels are made by etching a laminate partially through its thickness and stacking another laminate upon it to form a flow channel. Header holes through the laminate thickness are provided for inlets and outlets. Ashmead et al. suggest incorporating catalytic activity by packing a segment of a channel with catalytic beads or depositing catalytic materials onto the surface of a channel. Ashmead et al. further suggest mixer chambers formed by a half channel etched on the bottom of one laminate in combination with a half channel on the top of another laminate. A disadvantage of the construction of Ashmead et al. is the complexity and expense of carving laminates partially through the thickness of the laminates. A further disadvantage of the construction of Ashmead et al. is the small aspect ratio of width to depth of their channels for flow resistance and pressure drop. The construction of Ashmead et al. cannot achieve diffusive mass transfer, or controlled mixing by actuation.

Thus, there remains a need for a microchannel mass exchanger having a lower cost of fabrication and which provides a reduced pressure drop.

SUMMARY OF THE INVENTION

The present invention is a mass exchanger and method of making it. The method of making a microchannel mass exchanger, has the steps of:

(a) forming at least one inner thin sheet having a solid margin around a circumference, the solid margin defining a slot through a thickness;

(b) forming at least one outer thin sheet having at least two header holes positioned within the solid margin and positioned at opposite ends of a slot length, wherein the at least one inner thin sheet is placed adjacent the at least one outer thin sheet, the solid margin sealably spacing the at least one outer thin sheet, the at least one outer thin sheet defining at least one longitudinal wall of a flow channel having a length parallel to a thin sheet length, wherein a fluid enters through one of the header holes into the slot to flow in a direction parallel or longitudinal to the length of the flow channel and exits through another of the header holes;

(c) placing a mass transfer medium on at least one of the outer thin sheet within the solid margin;

(d) stacking the at least one inner thin sheet in contact with the at least one outer thin sheets into a stack and placing an end block on the at least one inner thin sheet as a pre-bonded assembly; and (e) bonding the pre-bonded assembly into the microchannel mass exchanger.

The apparatus of the present invention is a microchannel mass exchanger, having:

(a) at least one inner thin sheet having a solid margin around a circumference, the solid margin defining a slot through a thickness;

(b) at least one outer thin sheet having at least two header holes positioned within the solid margin and positioned at opposite ends of a slot length, wherein the at least one inner thin sheet is placed adjacent the at least one outer thin sheet, the solid margin sealably spacing the at least one outer thin sheet,the at least one outer thin sheet defining at least one longitudinal wall of a flow channel having a length parallel to a thin sheet length, wherein a fluid enters through one of the header holes into the slot to flow in a direction parallel or longitudinal to the length of the flow channel and exits through another of the header holes;

(c) a mass transfer medium on at least one of the at least one outer thin sheet within the solid margin;

(d) the at least one inner thin sheet in contact with the at least one outer thin sheets into a stack with an end block on the at least one inner thin sheet as a pre-bonded assembly; and (e) the pre-bonded assembly bonded into the microchannel mass exchanger.

An advantage of the present invention is that the slot may have a large aspect ratio of its width to its depth or thickness. Another advantage of the present invention is that it accommodates a variety of materials including materials not amenable to bulk or surface micromachining, for example ceramics. A further advantage is that the method may be used in high volume production which is a key to economical and commercially viable products.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWINGS

FIG. 2a is an exploded view of a stack of thin sheets forming a two-pass serpentine path once through mass exchanger.

FIG. 5a is an isometric view of an outer thin sheet with a mass transfer medium integral thereto.

FIG. 5b is a magnified view of the mass transfer medium.

FIG. 5c is a side view of an inner thin sheet with a perforated mass transfer medium.

FIG. 5d is a side view of an inner thin sheet with an offset perforated mass transfer medium.

DESCRIPTION OF THE PREFERRED EMBODIMENT(S)

Figure 1A:
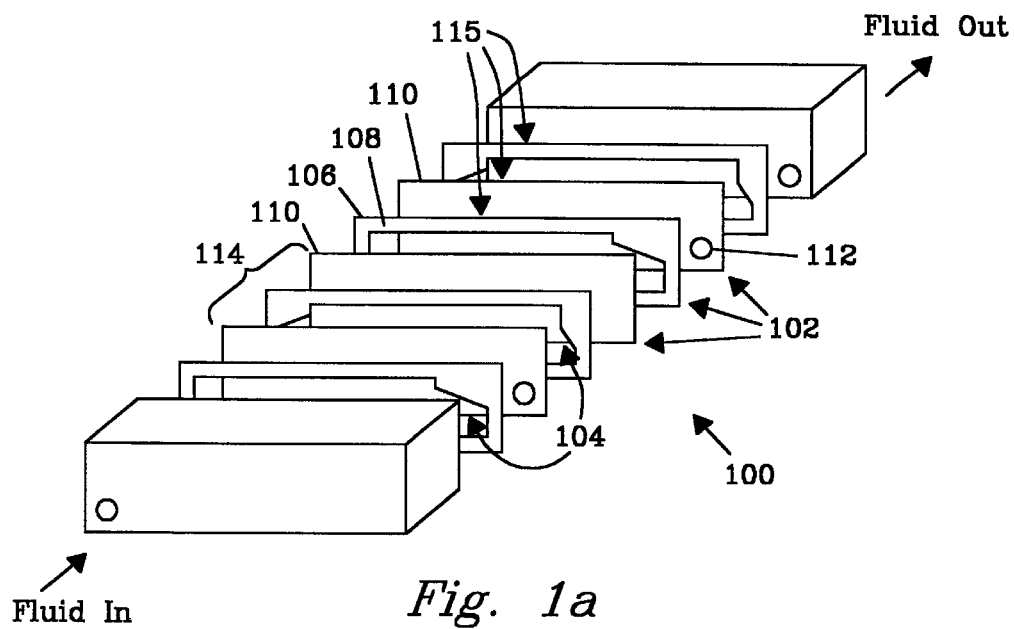
FIG. 1a is an exploded view of a stack of thin sheets forming a one-pass serpentine path once through mass exchanger.

Referring to FIGS. 1a and 2a, two embodiments of the present invention of a once through mass exchanger 100 are shown. Common to both embodiments are (a) at least two thin sheets 102 stacked and bonded to form at least one flow channel 104. The plurality of thin sheets 102 has subcategories of (b) at least one inner thin sheet 106, each having a solid margin 108 around a circumference, the solid margin 108 defining a slot 104 through a thickness; and (c) at least one outer thin sheet 110, each having at least two header holes 112 positioned within the solid margin 108 and positioned at opposite ends of a slot length L1. Each of the inner thin sheets 106 may be sandwiched between a pair of the outer thin sheets 110 to form a closed flow channel assembly 114 wherein fluid enters through one of the header holes 112 into the slot 104 and exits through another of the header holes 112.

When each of the inner thin sheets 106 is sandwiched between a pair of the outer thin sheets 110, the solid margin 108 sealably spaces the outer thin sheets 110 and the outer thin sheets 110 define longitudinal walls of a flow channel 104 with a length L-1 parallel to a thin sheet length L-2, wherein a fluid enters through one of the header holes 112 into the slot 104 to flow in a direction parallel or longitudinal to the length L-2 of the flow channel 104 and exits through another of the header holes 112. Aspect ratios of the width W of the slot 104 to the thickness range from about 10 to about 100.

The stacked plurality of thin sheets 102 define an outer surface defined by a plurality of edge thicknesses 115 of the stacked plurality of thin sheets 102. The outer surface may be proximate a thermal load 150 so that the thermal load (heat or cool) is transmitted via conduction through the stacked plurality of thin sheets 102 margin and also transmitted via convection between the stacked plurality of thin sheets 102 and the fluid in the flow channel 104.

Figure 1B:
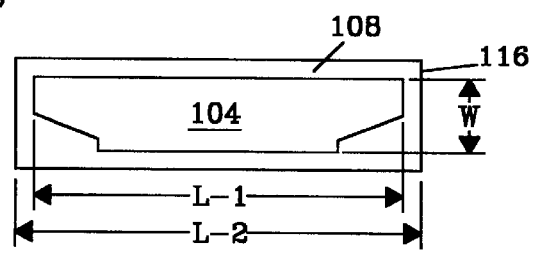
FIG. 1b is a side view of an inner thin sheet with no header holes.
Figure 1C:
FIG. 1c is a side view of an outer thin sheet with two header holes.
Figure 1D:
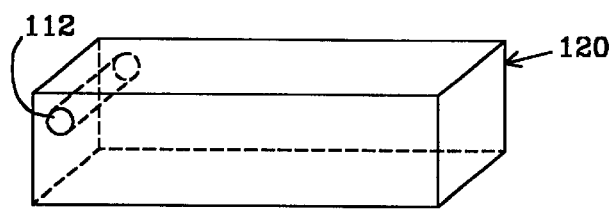
FIG. 1d is a side view of an end block with one header hole.
Figure 2B:
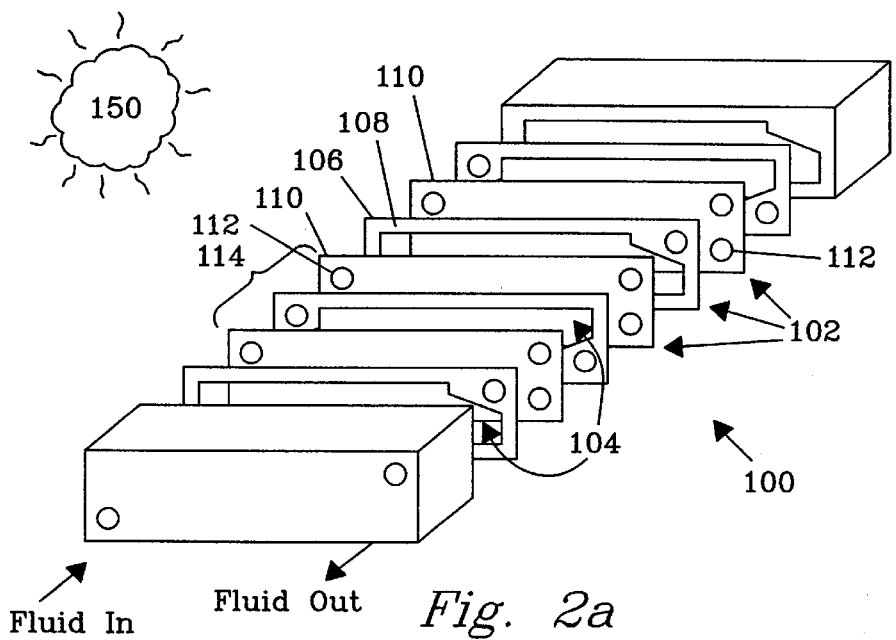
FIG. 2b is a side view of an inner thin sheet with two header holes.
Figure 2B:
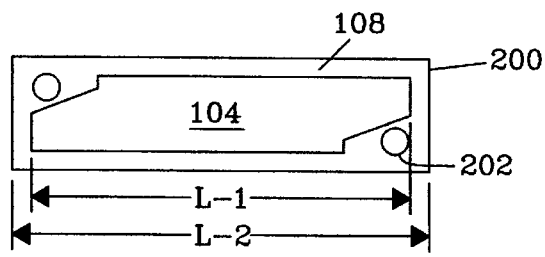
Figure 2C:
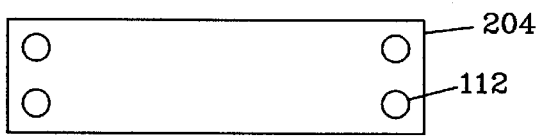
FIG. 2c is a side view of an outer thin sheet with four header holes.
Figure 2D:
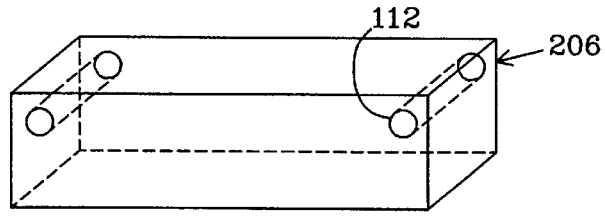
FIG. 2d is a side view of an end block with two header holes.

Distinctions between the embodiments are shown in FIGS. 1b, 1c, 1d, 2b, 2c, 2d. In FIG. 1b, the inner thin sheet 116 has the slot 104 defined by the solid margin 108 but no other features. In FIG. 2b, the inner thin sheet 200 has the slot 104 defined by the solid margin 108 and it has header holes 202. In FIG. 1c, the outer thin sheet 118 has two header holes 112 whereas in FIG. 2c, the outer thin sheet 204 has four header holes 112. In FIG. 1d, the end block 120 has one header hole 112 for an inlet on one end and an outlet on the opposite end, whereas in FIG. 2d, the end block 206 has two header holes 112 so that the inlet and outlet are on the same end. In operation, the embodiment of FIGS. 1a, 1b, 1c and 1d has a single fluid that passes through sequential inner thin sheets 116 in a serpentine path. In the embodiment of FIGS. 2a, 2b, 2c, and 2d, the single fluid passes through every other inner thin sheet 200 in a serpentine path then reverses and passes through the alternating inner thin sheets 200 in a reverse serpentine path. In both embodiments, the single fluid passes through each inner thin sheet 106 once.

The flow channels 104 may be any length or width (e.g. 5 cm×1 cm), but must have a thickness less than about 0.015 cm to achieve the enhanced mass transfer coefficients characteristic of microchannels.

The material(s) of construction may be the same for each element or varied. In a preferred embodiment, the material(s) of construction is the same for each element to facilitate bonding and sealing of the elements one to another. Materials include but are not limited to metals, for example stainless steel or copper, plastics, and ceramics.

A dual fluid embodiment is shown in FIGS. 3a, 3b, 3c, 3d, 3e. Fins may be made, if desired for facilitating heat transfer to or from the outer surface, by offsetting the alignment of slots 104 and header holes 112.

Figure 3A:
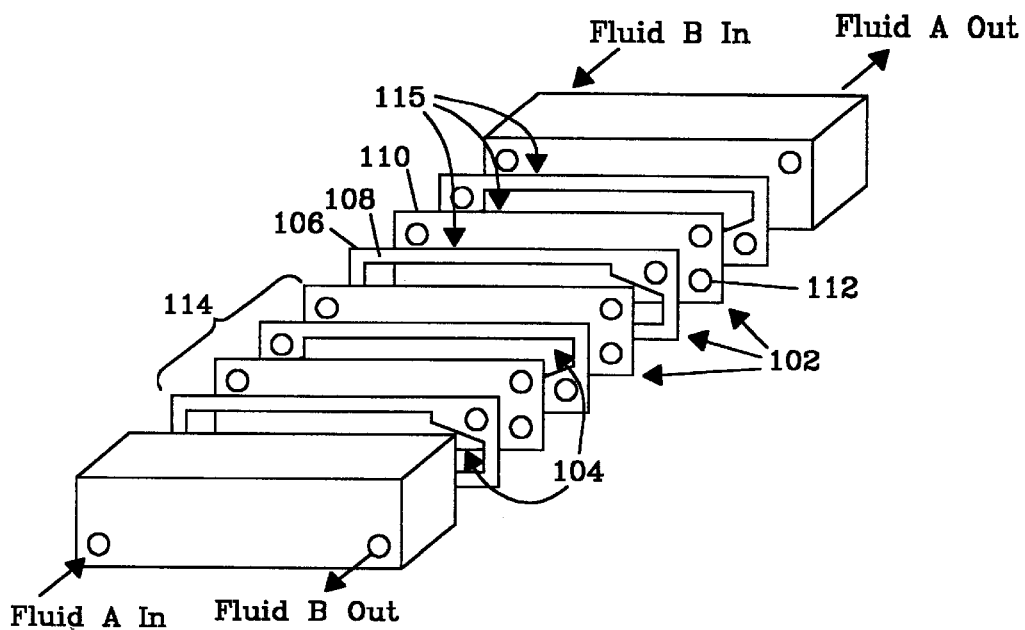
FIG. 3a is an exploded view of a dual fluid microchannel mass exchanger.
Figure 3B:
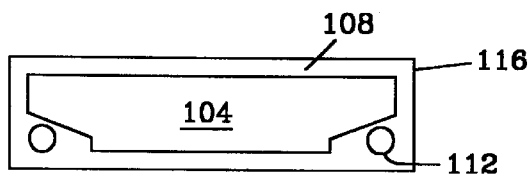
FIG. 3b is a side view of an inner thin sheet with two header holes on one side of the inner thin sheet.
Figure 3C:
FIG. 3c is a side view of an outer thin sheet with four header holes.
Figure 3D:
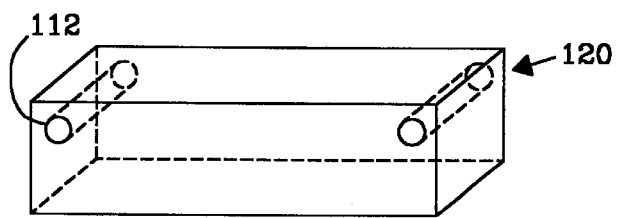
FIG. 3d is a side view of an end block with two header holes.
Figure 3E:
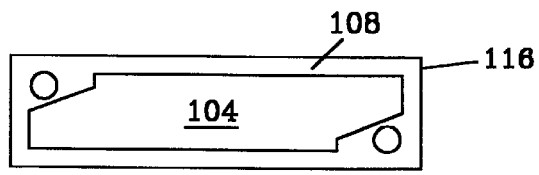
FIG. 3e is a side view of an inner thin sheet with two header holes on diagonal corners of the inner thin sheet.
Figure 3F:
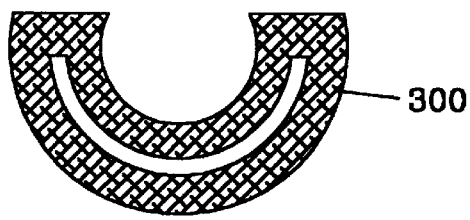
FIG. 3f is a side view of a semi-circular inner thin sheet.
Figure 3G:
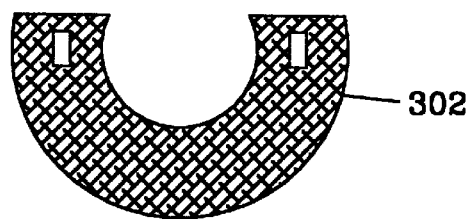
FIG. 3g is a side view of a semi-circular outer thin sheet.
Figure 3H:
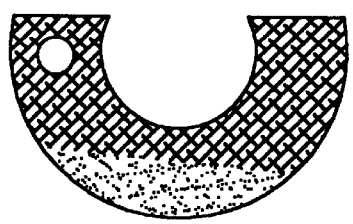
FIG. 3h is a side view of a semi-circular end block.

Further geometric arrangements are shown in FIGS. 3f, 3g, 3h. FIG. 3f shows an inner thin sheet 300 that has a semi-circular side view. FIG. 3g shows an outer thin sheet 302 that has a semi-circular side view, and FIG. 3h shows an end block that has a semi-circular side view. A semi-circular design permits compact construction around other system components, for example a pipe or electrical chase. Of course, other non-linear geometries may be used.

Bonding of metallic laminates may be by brazing, soldering, or diffusion bonding. Each laminate is cleaned to remove any oxide coating that would interfere with bonding. A preferred method of cleaning is with an acid rinse. The pre-bonded assembly or stack is compressed in a jig and heated under vacuum. For copper, the temperature is about 630° C. at a pressure of 6000 psi for about 4 hours to achieve a reliable diffusion bond. For aluminum, 350° C., 10,000 psi for 2 hours; and for stainless steel type 304, 600° C., 6000 psi for 2 hours.

The mass transfer medium may be a solid material, for example catalyst, absorbent material, adsorbent material, hydrophobic layer, hydrophilic layer, or combination thereof. The mass transfer medium may also be a porous or perforated material, wherein the term "porous material" refers to material through which diffusion occurs but bulk flow or "weeping" flow is prevented. When the pores or holes are of a size to permit bulk flow or weeping, the mass transfer medium is referred to herein as a perforated material. The porous or perforated material may also be a solid material or have a solid material thereon. A perforated material may be used for mixing two streams. An alternative form of mass transfer medium is a self assembling monolayer bonded to the surface of the outer thin sheet 118 within the margin 108, or bonded within the pores of a porous or perforated sheet wherein the self assembling monolayer further has one or more functional groups that would contact a fluid. The mass transfer medium may include active microcomponents, for example micro-propellers for imparting motion to a fluid.

For attachment of a self assembling monolayer, it may be necessary to coat a surface with an oxide material, for example silica, titania, or zirconia. Organic molecules useful as self assembling monolayers include silane, for example chlorosilane, alkoxysilane, and combinations thereof. Functional groups include but are not limited to mercaptan, mercaptan related compounds, amines, methyl, halogen, nitrile, pyradines, alkyls, polymers, and combinations thereof. For binding metals, tris(methoxy) mercaptopropysilane (TMMPS) has a thiol group with a high affinity for binding metals. Alternatively, therefore, using TMMPS on both ends of the organic molecule may permit attachment of the organic molecule directly to a metal outer thin sheet without a coating. By placing only hydroxyl functional groups on the organic molecule, water may be removed from a mixture to parts per trillion levels.

For example a mixture of oil and water may have the water removed in this manner. This may be especially useful for removing tritiated water from oil. Inorganic materials may be attached via self assembling monolayers as described in W091/17286 published Nov. 14, 1991, PROCESS FOR DEPOSITING THIN FILM LAYERS ONTO SURFACES MODIFIED WITH ORGANIC FUNCTIONAL GROUPS AND PRODUCTS FORMED THEREBY, hereby incorporated by reference. Briefly, a polymeric surface is sulfonated then exposed to a solution of metal ionic species so that the metal ionic species deposits on the sulfonated surface as a solid layer.

Alternatively, the mass transfer medium 500 may be a non-porous, solid catalyst or absorbent material.

Figure 4:
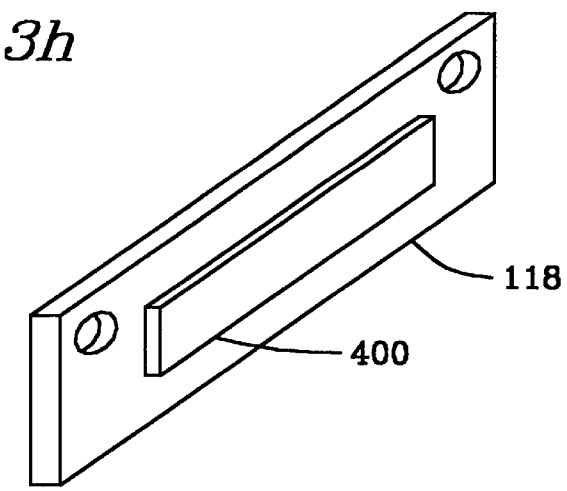
FIG. 4 is an isometric view of an outer thin sheet with a mass transfer medium bonded thereto.

The mass transfer medium may be in different forms as illustrated in FIGS. 4, 5a and 5b, and 5c, 5d, 5e. FIG. 4 shows the mass transfer medium as a solid material 400 bonded to an outer thin sheet 118. Alternatively, the catalyst material 400 may be bonded to an end block 120.

Another form of mass transfer medium is shown in FIGS. 5a and 5b wherein the mass transfer medium 500 is integral to the outer thin sheet 118 as a mass transfer sheet. In this form, the mass transfer medium 500 extends through the thickness of the outer thin sheet and deployed as sandwiched between a pair of inner thin sheets 116 and closed with a pair of end blocks 120. In FIGS. 5a and 5b, the mass transfer medium 500 is a porous material having pores 502 or holes either straight through the thickness or not straight as interconnected porosity.

Figure 5E:
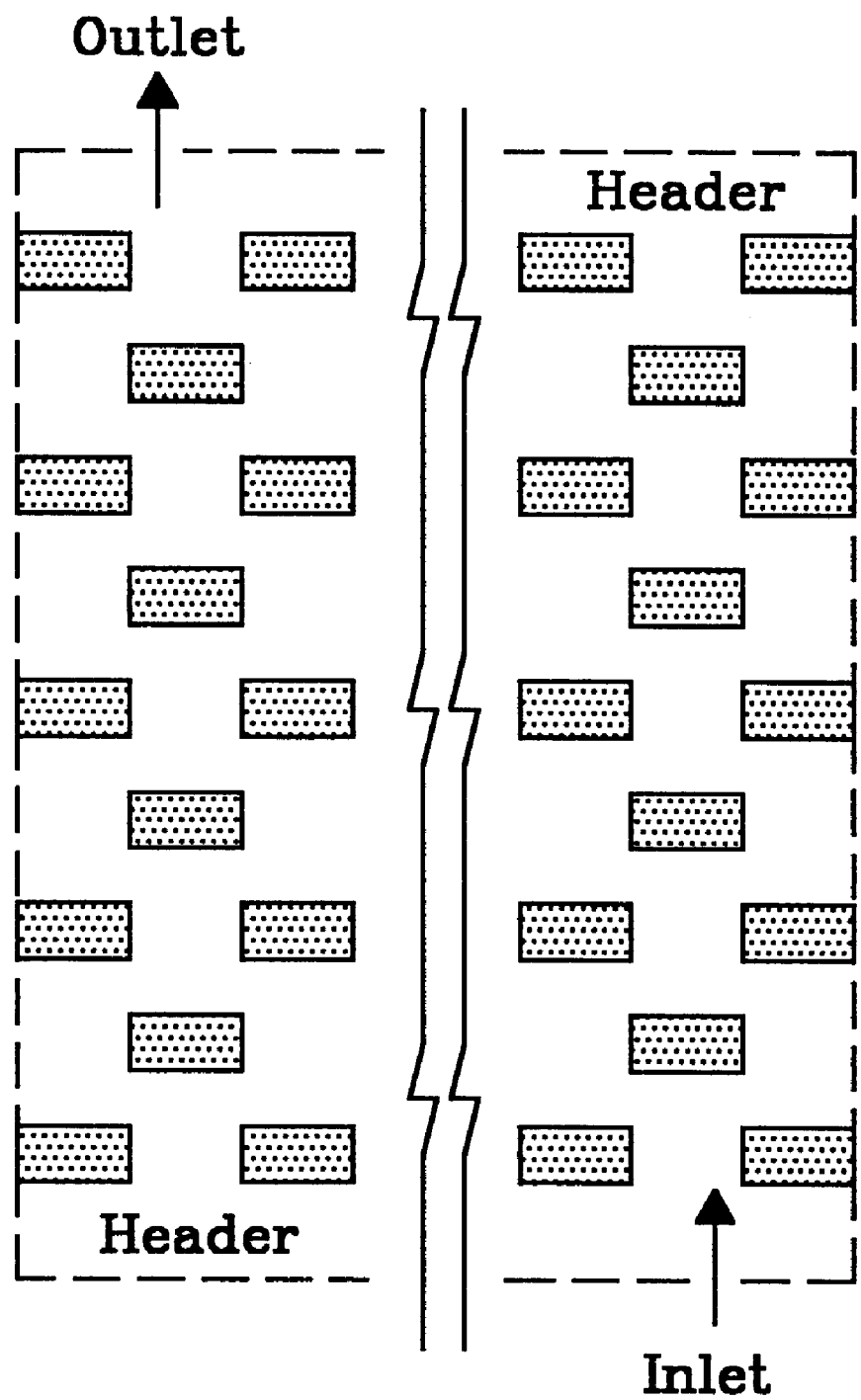
FIG. 5e is a cross section of an assembly of perforated inner thin sheets with outer thin sheets therebetween.

Yet another form of mass transfer medium is shown in FIGS. 5c, 5d and 5e. Outer thin sheet 504 has ribs 506 defining slots 508 as a perforated material. In FIG. 5d, outer thin sheet 510 has ribs 512 defining slots 514 that are offset compared to those of outer thin sheet 504. Upon alternate stacking of these outer thin sheets 504, 510 with inner thin sheets 116 therebetween, the cross section shown in FIG. 5e is obtained which is useful for mixing two streams.

Chemical Separations and Conversions

Chemical separations as used herein includes any exchange of a compound or element from one solvent to another where the solvents may be liquid or gas or both. An example is an absorption cycle refrigeration system. In chemical separations, a mass transfer medium 500 in the form of a porous membrane is selected so that a first solvent containing the element or compound does not wet the porous membrane but a second solvent wets the porous membrane and the element or compound in the first solvent transfers to the second solvent and through the porous membrane.

By making the depths of the solvents small, i.e. less than about 1 micron, higher absorption rates are achieved than with larger depths. A microporous contactor unit may be a microporous contactor sheet as shown in FIG. 5 placed between cover sheets. Each cover sheet has a microplenum or at least one microcomponent together with an inlet and an outlet permitting fluid flow across the microporous contactor sheet. A microplenum may be formed with an inner thin sheet 116 in combination with an end block 120.

In most practical systems, to achieve high absorption/desorption rates, heat will need to be transferred either to or from the absorption/desorption fluids. Accordingly, heat transfer may be combined with the microporous contactor unit.

The pores are preferably as small as practical, on the order of a few microns, i.e. less than about 10 microns, and most preferably less than about 3 microns. The small pore size provides a strong resistance to a through-sheet velocity or pressure gradient. A cover or combination of inner thin sheet 116 with end block 120 is placed over the outer thin sheet having the porous material. A fluid plenum may thereby be formed that is less than about 10 microns in height from the sheet to the cover. Mass diffusion then occurs within a stagnant film and through the microporous contactor sheet. Micro-components, for example microgrooves, may be manufactured on one or both sides of the microporous contactor sheet. Additionally, the microporous contactor sheet may have no microcomponents itself, but the cover sheet(s) may have microcomponents for directing fluid flow across the microporous contactor sheet. A further embodiment is simply a fluid microplenum on either side of the microporous contactor sheet.

The microporous contactor sheet may be made by micromachining a metal, ceramic or plastic by, for example Lithography, Galvanoformung (electrodeposition), Abformung (injection molding), laser micromachining, electrochemical micromachining, or sintering. Advantages of micromachined contactor sheets include precise control of the pore size throughout the sheet.

In operation, fluids may flow in parallel, counterflow, or crossflow. The parallel flow results in lesser mass flux or extraction, but permits lesser pressure differential or gradient across the microporous sheet. When gas is one of the fluids and the gas is to be absorbed into a liquid, it is preferred that the gas pass through the microporous sheet, but not the liquid. Accordingly, it is preferred that the microporous sheet either be coated so that the liquid does not wet the microporous sheet or have pores sufficiently small so that the liquid is supported by its surface tension and does not flow through the pores.

In the case wherein a microporous sheet is not sufficiently self supporting between the covers, the covers may be made with projections or lands for support of the microporous sheet. Alternatively, as previously discussed, the microporous sheet may have grooves or microcomponents. In either case, projections or lands would support the microporous sheet.

Figure 6:
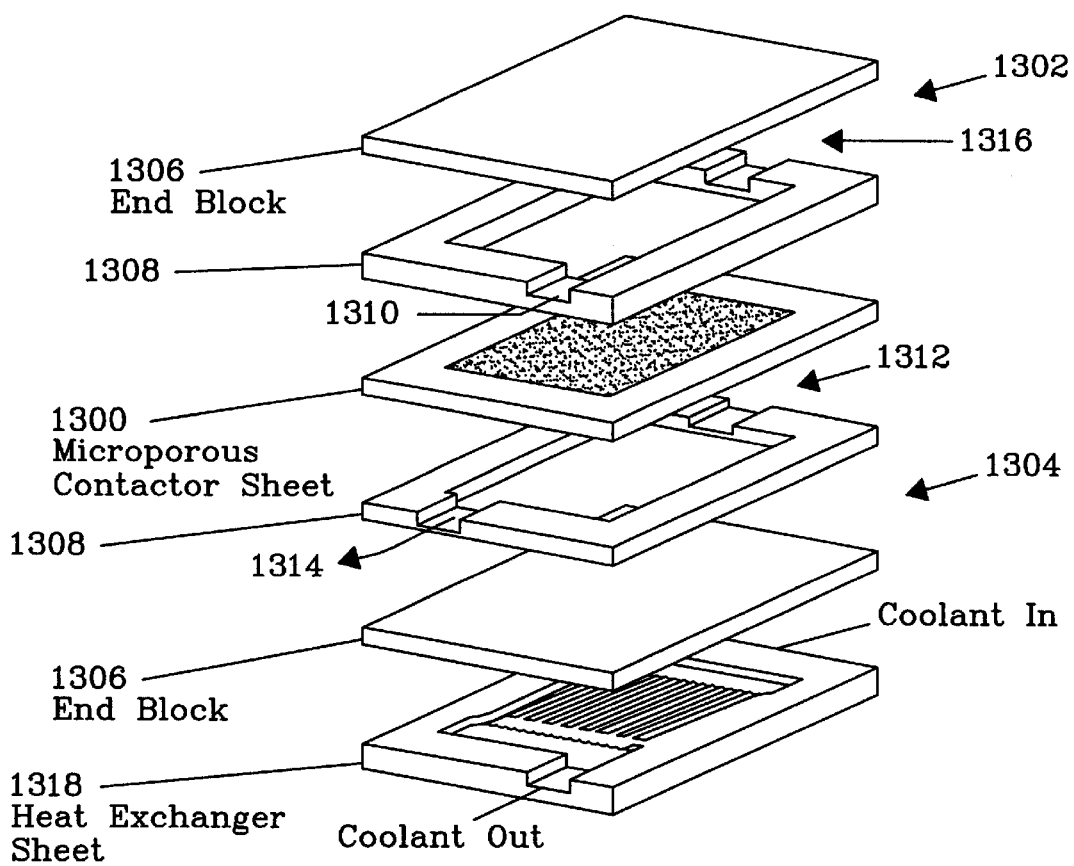
FIG. 6 is an exploded view of a microcomponent mass exchanger.

A microporous contactor unit is shown in FIG. 6. A microporous contactor sheet 1300 is placed between two covers 1302, 1304 each having an end block 1306 and an inner thin sheet 1308 that create microplena between the microporous contactor sheet 1300 and the end blocks 1306 upon assembly. Note in this embodiment, the inlet and outlet are through the side of the inner thin sheets 1308. When used as an absorber, a gas is introduced into cover 1302 through inlet 1310. A weak solution enters the cover 1304 through inlet 1312 and the strong solution exits through outlet 1314. When used for solvent extraction, the solvent enters the cover 1302 at inlet 1310 and extract exits outlet 1316. Feed enters inlet 1312 and raffinate exits from outlet 1314. For either absorption or solvent extraction, if heat must be removed or added, a microchannel heat exchanger sheet 1318 may be used as shown. When used as a chemical reactor, specifically for partial oxidation of liquid organics, the gas is oxygen that passes through the microporous contactor sheet 1300.

EXAMPLE 1

An experiment was conducted to demonstrate separation in the form of gas absorption into a liquid. More specifically, ammonia vapor was absorbed into liquid water. A microporous contactor sheet made of sintered stainless steel having a nominal thickness of 4 mm (1/16 inch), average pore size of 2–5 micron and a porosity of from 30% to 50%. Cover sheets provided microplena having a thickness or distance from the microporous contactor sheet to the inside surface of the cover sheet (film thickness) ranging from about 100 to 300 microns. Within the liquid film on the microporous contactor, the ammonia was absorbed into the water. Ammonia flow rate varied from 0–4 g/min with water flow rate ranging from 0–33 g/min. Temperature ranged from 20–60° C. for isothermal and adiabatic test runs. Absorption pressure was from 15 to 30 psia.

Figure 7:
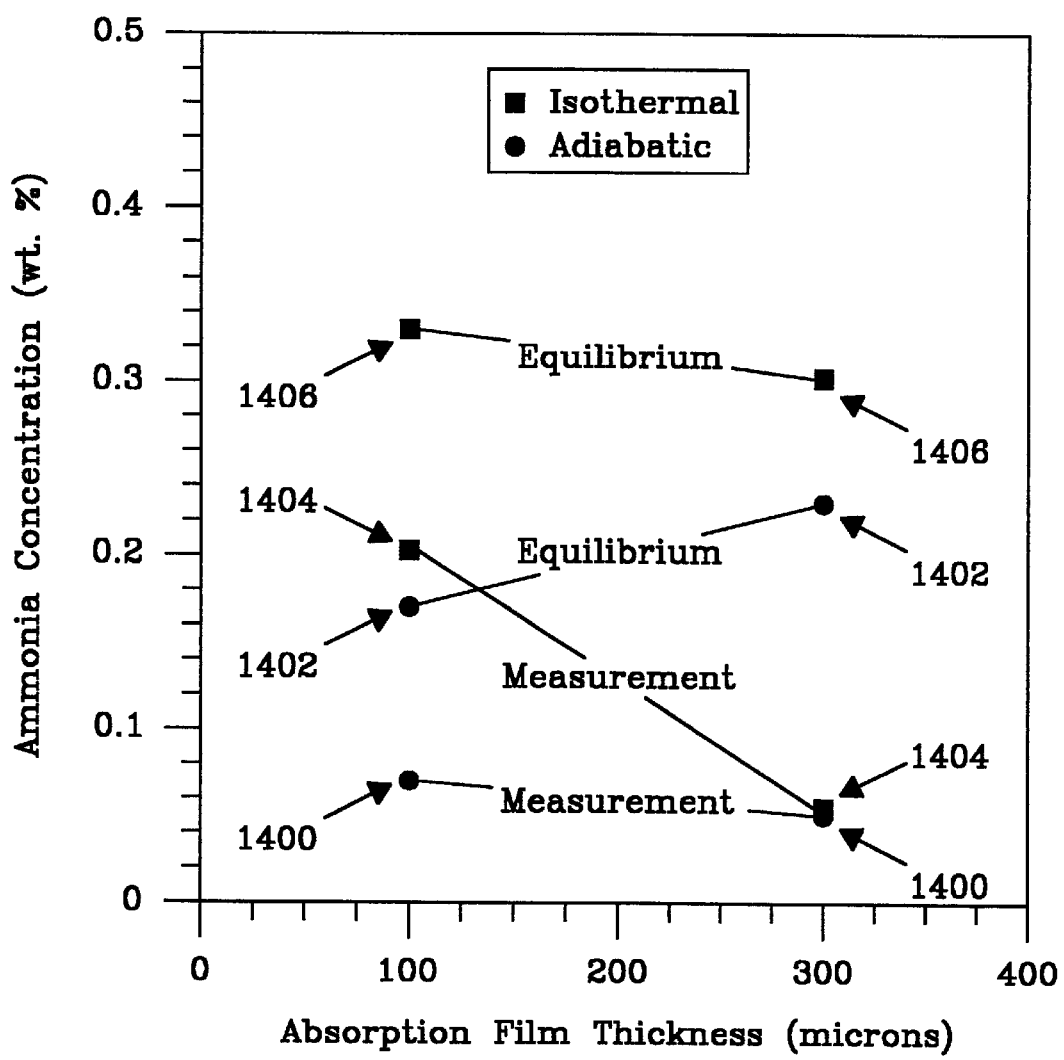
FIG. 7. is a graph of ammonia concentration versus absorption film thickness for Example 1.

Results are shown in FIG. 7. Considering first the measured data for the adiabatic test, the points 1400 represent actual measurements of ammonia concentration at film thicknesses of 100 and 300 microns. The theoretical maximum absorption or "equilibrium" (which is a function of temperature) was calculated and represented by point 1402 for the adiabatic test. As the absorption film thickness is decreased, the measured ammonia concentration approaches the theoretical maximum.

Similar results are shown for the isothermal test represented by actual measurement points 1404 and equilibrium points 1406. Had the test been truly isothermal, the equilibrium line would have been horizontal. The slight slope of that line indicates a difference in temperature at the different film thicknesses.

Comparing the adiabatic data and the isothermal data, it is clear that greater absorption is achievable with heat removal (isothermal) than with no heat removal (adiabatic).

Porous or Perforated Material Fabrication

Stainless steel porous material or membranes were produced using commercial photochemical machining at Microphoto, Inc., Roseville, Mich. The porous material was very clean, well defined, had no burrs, and excellent part to part reproducibility. However, this process is limited to producing holes of a diameter no smaller than the thickness of the sheet. We made a perforated sheet with holes of about 100 micrometers in diameter spaced 250 micrometers apart on 50 micrometer thick stock.

Using a 50 micrometer thick polyimide (Kapton) sheet, holes of 15 micrometer diameter were individually laser drilled in a 15×15 square pattern on a 35 micrometer spacing. An overall matrix was 10 mm×80 mm. The laser micromachining system was a Potomac model LMT-4000 using a 248-nm KrF excimer laser (Potomac model TGX-1000). The laser ran 75 msec per location at 2-KHz pulse rate (0.045 mJ/pulse) and no aperture in the beam. Total machine time to produce the matrix was nearly 45 hours.

A polymer porous material was also made using a mask patterning process. A commercial excimer laser machine (Resonetics, Inc., Nashua, N.H.) had a rectangular beam profile (about 8 mm×about 25 mm) permitting multiple holes at a time to be made through a mask, significantly reducing overall machining time. Holes of 31 micrometer diameter spaced 61.5 micrometer in a 10 mm×80 mm matrix were made in about 20 minutes. The KrF excimer laser (248 nm) had a pulse energy of 257 mJ and pulse rate of 100 Hz was used.

In assemblies using polymer porous materials, it is possible to use metal inner thin sheets and outer thin sheets, but bonding would be by clamping or bolting, relying on the polymer margin for sealing. Alternatively, the inner thin sheets and outer thin sheets may be a polymer as well wherein the entire assembly could be heat or chemically bonded.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A microchannel mass exchanger, comprising a laminate bonded from sheets comprising:
   (a) a first cover sheet comprising a microplenum or at least one microcomponent and further comprising an inlet and an outlet;
   (b) a contactor sheet comprising a porous or perforated material; and
   (c) a second cover sheet comprising a microplenum or at least one microcomponent and further comprising an inlet and an outlet;
   wherein the contactor sheet is disposed between the first and second cover sheets; and
   wherein, during operation, an element or compound disposed between the contactor sheet and first cover sheet can flow across the contactor into a space between the contactor and the second cover sheet.

2. The microchannel mass exchanger of claim 1 wherein said first and second cover sheets each comprise an end block and an inner sheet, wherein each inner sheet comprises a solid margin around the circumference of each inner sheet; and
   wherein the inner sheets space the contactor sheet and the end blocks, thus creating microplena between the end blocks and the contactor sheet.

3. The microchannel mass exchanger of claim 2 wherein the contactor sheet comprises a porous material.

4. The microchannel mass exchanger of claim 3 wherein the porous material has an average pore size of less than about 10 microns.

5. The microchannel mass exchanger of claim 3 wherein the porous material comprises a microporous material and wherein at least one of said cover sheets comprise projections or lands that support said contactor sheet.

6. The microchannel mass exchanger of claim 3 wherein the microplena have thicknesses of about 100 to 300 micrometers.

7. The microchannel mass exchanger of claim 3 wherein at least one of said microplena has a thickness that is less than about 10 microns.

8. The microchannel mass exchanger of claim 3 wherein each inner sheet comprises an inlet and an outlet through the side of said inner sheet.

9. The microchannel mass exchanger of claim 3 further comprising a microchannel heat exchanger sheet capable of adding heat or removing heat from said microchannel mass exchanger.

10. The microchannel mass exchanger of claim 3 wherein a gas occupies the plenum between the first cover layer and the contactor sheet, and a liquid is present the plenum between the second cover layer and the contactor sheet, and further wherein the gas passes through the contactor sheet, but the liquid does not pass through the contactor sheet.

* * * * *